(12) United States Patent
North et al.

(10) Patent No.: US 7,603,178 B2
(45) Date of Patent: Oct. 13, 2009

(54) ELECTRICAL STIMULATION LEAD, SYSTEM, AND METHOD

(75) Inventors: Richard B. North, Baltimore, MD (US); Terry D. Daglow, Allen, TX (US); Stephen L. Goldman, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 640 days.

(21) Appl. No.: 11/279,712

(22) Filed: Apr. 13, 2006

(65) Prior Publication Data

US 2007/0060991 A1 Mar. 15, 2007

Related U.S. Application Data

(60) Provisional application No. 60/671,977, filed on Apr. 14, 2005.

(51) Int. Cl.
*A61N 1/05* (2006.01)
(52) U.S. Cl. .................................................. 607/117
(58) Field of Classification Search ................. 607/117, 607/116, 148, 152; 600/373–381, 393
See application file for complete search history.

(56) References Cited

U.S. PATENT DOCUMENTS 5,683,444 A 11/1997 Huntley
6,236,892 B1 5/2001 Feler
6,556,873 B1 4/2003 Smits
2004/0039434 A1 2/2004 Schrom et al.
2004/0176831 A1 9/2004 Gliner et al.
2004/0210291 A1 10/2004 Erickson et al.
2004/0249429 A1 12/2004 Tadlock

OTHER PUBLICATIONS

ISA/US, Commissioner for Patents, International Search Report mailed May 25, 2007 for PCT/US06/14351.

*Primary Examiner*—Mark W Bockelman
(74) *Attorney, Agent, or Firm*—Craig Hoersten; Christopher S. L. Crawford; Peter Lando

(57) ABSTRACT

In one embodiment, a paddle lead comprises: a plurality of stimulating electrode contacts disposed, the plurality of stimulation electrode contacts being adapted to allow the stimulation paddle to flex transversely about a longitudinal axis; wherein the plurality of stimulation electrode contacts are arranged in at least first, second, and third rows that are disposed perpendicular to a longitudinal axis of the paddle; the first and third rows respectively having multiple electrode contacts electrically coupled to different conductors of the lead to enable the multiple electrode contacts of the first and third rows to function in independent cathode states, anode states, or high-impedance states; the second row being disposed between the first and third rows, the second row having multiple electrode contacts each electrically coupled to a common conductor to cause the multiple electrode contacts of the second row to function in a common cathode state, anode state, or high-impedance state.

22 Claims, 5 Drawing Sheets

ELECTRICAL STIMULATION LEAD, SYSTEM, AND METHOD

RELATED APPLICATION

This application claims the benefit of U.S. Provisional Patent Application Ser. No. 60/671,977, filed Apr. 14, 2005, entitled "ELECTRICAL STIMULATION LEAD, SYSTEM, AND METHOD," which is incorporated herein by reference.

TECHNICAL FIELD

The present application is generally related to electrical stimulation for medical purposes and, in particular, to an electrical stimulation lead, system, and method.

BACKGROUND

Electrical energy may be applied to a person's spinal cord to treat a variety of clinical conditions, such as chronic pain. For example, electrical energy may be applied to the spinal cord to cause a subjective sensation of numbness or tingling in an affected region of the body, known as "paresthesia." The electrical energy is delivered through stimulating electrodes positioned proximate the spinal cord tissue targeted for stimulation. The stimulation electrodes may be carried by either two primary vehicles: a percutaneous lead or a laminotomy, surgical, or "paddle" lead. Percutaneous leads are positioned using a needle that is passed through the skin and into the epidural space adjacent the spinal cord such that the stimulating electrodes are proximate nerve tissue targeted for stimulation. Percutaneous leads deliver energy generally radially in all directions because of the circumferential nature of the stimulation electrodes. Paddle leads have a paddle-like configuration and typically have a number of directional stimulation electrodes arranged in one or more columns. Paddle leads may provide more focused energy delivery than percutaneous leads because the directional stimulating electrodes may be present on only one surface of the lead. Paddle leads may be desirable in certain situations because they may provide more direct stimulation to targeted nerve tissue and may require less energy to produce a desired effect. Directional stimulating electrodes of paddle leads may be arranged to provide anode guarding or blocking to more specifically direct stimulation to targeted nerve tissue.

SUMMARY

The electrical stimulation lead, system, and method of some embodiments of the invention may reduce or eliminate certain problems and disadvantages associated with prior techniques for electrically stimulating spinal cord tissue.

According to one aspect, an electrical stimulation portion adapted for implantation in a person's body to provide therapeutic electrical stimulation of target spinal cord tissue includes a plurality of stimulating electrode contacts that are integrated on a first face of the stimulation portion and are adapted for implantation in the person's body with the stimulating portion. The plurality of stimulation electrode contacts are operable to provide electrical stimulation to target spinal cord tissue. The plurality of stimulation electrode contacts comprise at least one stimulating electrode contact having a first contact area and at least one traverse array of stimulating electrode contacts. Each traverse array comprises a plurality of stimulating electrode contacts aligned in a row and spaced apart from each other in a direction approximately perpendicular to a longitudinal axis of the stimulation portion. Each of the stimulating electrode contacts of the at least one traverse array have a second contact area no greater than three-fourths of the first contact area. The stimulation portion includes one or more terminals each coupled to one or more respective stimulating electrode contacts of the plurality of stimulating electrode contacts and adapted to transmit electric current to its one or more respective stimulating electrode contacts.

Particular embodiments may provide one or more advantages. For example, some embodiments provide an electrical stimulating portion having a transverse array of stimulating electrode contacts that are aligned in a row in a direction perpendicular to a longitudinal axis of the stimulation portion and that are smaller than other stimulating electrode contacts of the lead to increase the ability of the stimulating portion to flex or bend transversely about the longitudinal axis of the stimulation portion. In addition, some embodiments include a plurality of grooves on an opposite face of the stimulating portion that provide further flexibility. The increased ability of the stimulating portion to flex or bend transversely about a longitudinal axis of the stimulating portion enables an operator of the stimulating portion to more easily implant and position the stimulating portion without damaging the lead or spinal cord tissue. This also increases comfort to the patient during use.

In one embodiment, a paddle lead comprises: a plurality of stimulating electrode contacts disposed on a first side of a stimulation paddle of the stimulation lead, the plurality of stimulation electrode contacts being adapted to allow the stimulation paddle to flex transversely about the longitudinal axis; a plurality of conductors for conducting electrical energy to the plurality of stimulating electrode contacts; wherein the plurality of stimulation electrode contacts are arranged in at least first, second, and third rows that are disposed perpendicular to a longitudinal axis of the stimulation paddle; the first and third rows respectively having multiple electrode contacts electrically coupled to different conductors of the plurality of conductors to enable the multiple electrode contacts of the first and third rows to function in independent cathode states, anode states, or high-impedance states; the second row being disposed between the first and third rows, the second row having multiple electrode contacts each electrically coupled to a common conductor of the plurality of conductors to cause the multiple electrode contacts of the second row to function in a common cathode state, anode state, or high-impedance state.

The foregoing has outlined rather broadly certain features and/or technical advantages in order that the detailed description that follows may be better understood. Additional features and/or advantages will be described hereinafter. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

For a more complete understanding of some embodiments of the invention and advantages thereof, reference is now made to the following description taken in conjunction with the accompanying drawings.

DETAILED DESCRIPTION

According to one representative embodiment, a neurological stimulation system 10 is used to electrically stimulate target tissue in a person's spinal cord to treat one or more clinical conditions, such as chronic pain. In general, an electrical stimulation lead with stimulation electrodes that include stimulating electrode contacts is implanted subcutaneously such that the stimulation electrode contacts are located proximate the target spinal cord tissue. As used herein, the term "proximate" means on, in, adjacent, or near. Thus, the stimulation electrode contacts of a stimulation lead are adapted to be positioned on, in adjacent, or near the target spinal cord tissue. In general, the stimulation electrode contacts proximate the spinal cord tissue deliver electrical stimulation pulses to the tissue, which thereby permanently or temporarily eliminates, reduces, or otherwise treats the one or more clinical conditions. This may in turn significantly increase the person's quality of life.

Figure 1A:
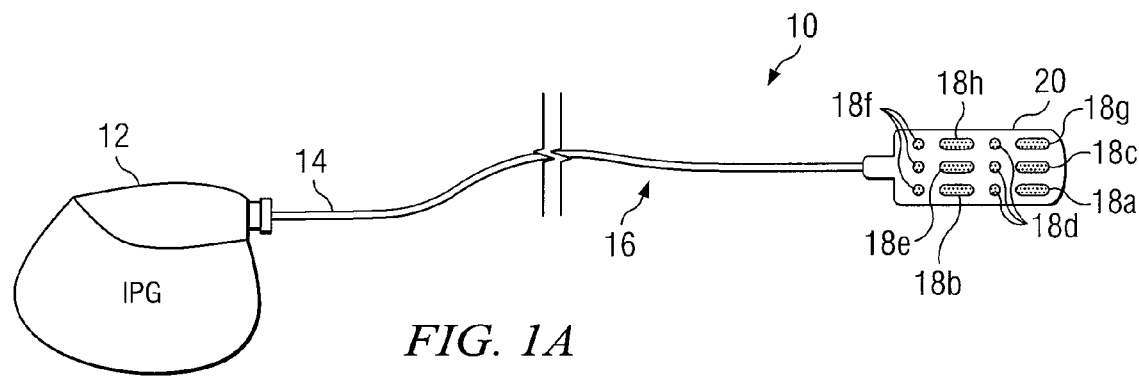
FIGS. 1A-1B depict example neurological stimulation systems for electrically stimulating a person's spinal cord tissue to treat one or more clinical conditions.
Figure 1B:
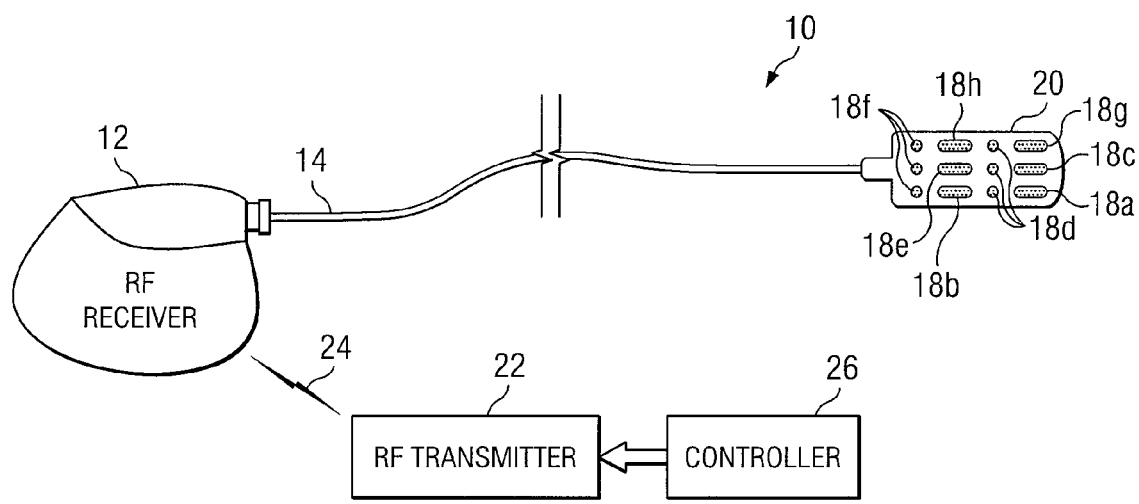

FIGS. 1A-1B illustrate example neurological systems 10 for electrically stimulating target spinal cord tissue to treat one or more clinical conditions, such as chronic pain. In general terms, stimulation system 10 includes a stimulation pulse generating portion (for example, implantable electrical stimulation source 12) and one or more implantable stimulation pulses to the target spinal cord tissue. In operation, both of these primary components are implanted in the person's body. In certain embodiments, stimulating source 12 is coupled directly to a connecting portion 16 of stimulation lead 14. In certain other embodiments, stimulating source 12 is not coupled directly to stimulating lead 14. For example, in a microstimulator, a stimulation source 12 instead is integrated and communicates with a stimulating portion, that may incorporate, one or more electrodes to the stimulating portion. One example in the art of such a microstimulator is the Bion® microstimulator manufactured by Advanced Bionics Corporation, while other microstimulators are known. Whether stimulation source 12 is coupled directly or indirectly to stimulation lead 14, stimulation source 12 controls the stimulation pulses transmitted to one or more stimulation electrodes 18 located on a stimulation portion 20 of stimulation lead 14, positioned proximate the target spinal cord tissue, according to suitable stimulation parameters (e.g., duration, amplitude or intensity, frequency, pulse width, etc.). A doctor, the patient, or another user of stimulation source 12 may directly or indirectly input stimulation parameters to specify or modify the nature of the stimulation provided to the patient.

In one embodiment, as shown in FIG. 1A, stimulation source 12 includes an implantable pulse generator (IPG). An example IPG may be incorporated in the Genesis® system or the Eon® system manufactured by Advanced Neuromodulation Systems, Inc. In another embodiment, as shown in FIG. 1B, stimulation source 12 includes an implantable wireless receiver. An example wireless receiver may be one incorporated in the Renew® system manufactured by Advanced Neuromodulation Systems. The wireless signals are represented in FIG. 1B by wireless link symbol 24. A doctor, the patient, or another user of stimulation source 12 may use a controller 26 located external to the person's body to provide control signals to wireless transmitter 22, wireless transmitter 22 transmits the control signals and power to the wireless receiver of stimulation source 12, and stimulation source 12 uses the control signals to vary the stimulation parameters of stimulation pulses transmitted through stimulation lead 14 to the target spinal cord tissue. An example of wireless transmitter 22 may be one incorporated in the Renew® system manufactured by Advanced Neuromodulation Systems.

Although specific stimulation systems have be provided as examples, any appropriate circuitry can be employed to generate suitable stimulation pulses for electrically stimulating the target spinal cord tissue using leads 14 according to some representative embodiments. Example of suitable circuitry for generating stimulation pulses is described in U.S. Pat. No. 6,609,031, which is hereby incorporated by reference as if fully illustrated and described herein.

Figure 2A:
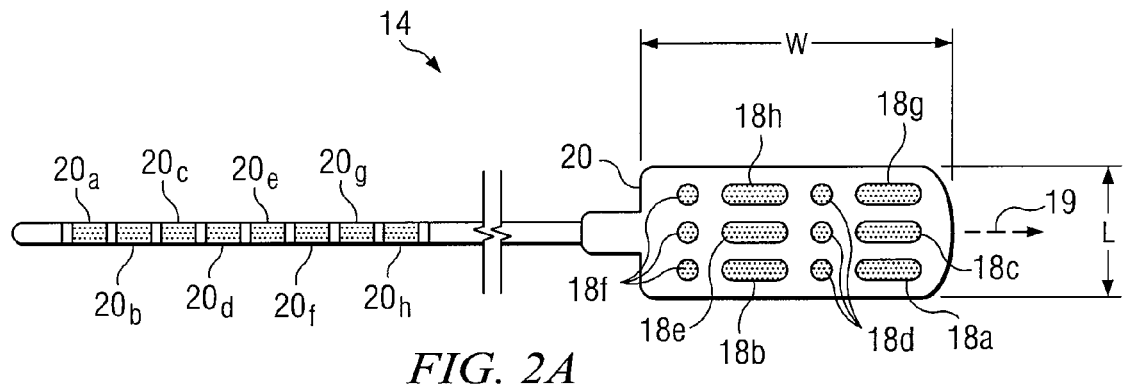
FIGS. 2A-2C illustrate an example stimulation lead that may be used to electrically stimulate a person's spinal cord tissue to treat one or more clinical conditions.

FIG. 2A illustrates an example stimulation lead 14 that may be used for electrically stimulating nerve tissue in a person's spinal cord to treat one or more clinical conditions, such as chronic pain. As described above, stimulation lead 14 includes stimulation electrodes 18. Each stimulation electrode 18 includes one or more stimulation electrode contacts adapted to be positioned proximate target spinal cord tissue and used to deliver to the target spinal cord tissue stimulation pulses received from stimulation source 12. Stimulation lead 14 may be referred to as a laminotomy, surgical, or paddle stimulation lead. The electrode contacts forming electrodes 18 are spaced apart from one another along one surface of stimulation portion 20. In particular embodiments, electrode contacts are separated from each other by one or more insulative materials. An insulative material of a stimulation lead may comprise an insulating, dielectric, or other material having a lower conductivity that a metal or other material used for form the stimulation electrode contacts of stimulation lead 14.

Stimulation lead 14 also includes one or more terminals 20 coupled to stimulation source 12 (illustrated in FIGS. 1A and 1B). Each terminal 20 is also coupled to one or more electrode contacts using electrical conductors running through stimulation lead 14 to transmit stimulation pulses to the electrode contacts. As discussed below, in the illustrated embodiment, electrodes 18*d* and 18*f* each comprise three electrode contacts spaced apart from each other and separated by one or more insulative materials. In this case, one terminal 20 may be coupled to each of the three electrode contacts operatively set to function as one electrode 18*d* and 18*f*. For example, terminal 20*d* may be coupled to the three electrode contacts forming stimulation electrode 18d and terminal 20f may be coupled to the three electrode contacts forming stimulation electrode 18f. The selection of the particular electrode contacts forming particular electrodes 18 to which particular terminals 20 are coupled may be made in any suitable manner to satisfy the objectives in particular embodiments. As illustrated, the electrode contacts of stimulation lead 14 are set to function as eight separate electrodes (18a-18h). In some embodiments, each electrode contact of a stimulation lead may be set to operate as a separate electrode. For example, with respect to stimulating portion 20, each of the three electrode contacts of electrode 18d and each of the three electrode contacts of electrode 18f could be set to operate as separate electrodes. Thus, those six electrode contacts could operate as six separate electrodes. If each electrode contact of stimulation lead 14 were set to operate as a separate electrode (with corresponding changes in wiring and the number of terminals 20), then the illustrated stimulation lead 14 would have twelve separate electrodes.

Electrode contacts forming electrodes 18 emit electrical stimulation energy received from stimulation source 12 in a direction generally perpendicular to the surface of stimulation lead 14 on which they are located. In operation, at any particular time, each electrode 18 may be programmed, configured, or otherwise set as an anode (+), as a cathode (−), or in an "off" state. An electrical current "flows" from an anode to a cathode. Consequently, a range of simple to complex electrical fields can be created by setting electrode contacts in various combinations of anodes, cathodes, and "off" states.

In the illustrated embodiment, electrodes 18d and 18f each comprise a traverse array of three electrode contacts aligned in a row in a direction approximately perpendicular to longitudinal axis 19 of stimulation lead 14. Thus, stimulation electrode 18d comprises three separate electrode contacts connected to operate as one electrode, and stimulation electrode 18f comprises three separate electrode contacts connected to operate as one electrode. In the illustrated embodiment, the electrode contacts of the stimulation lead generally have an oblong shape. In addition, each electrode contact of electrodes 18d and 18f are approximately three-fourths the size (e.g., as measured by the surface area of the electrode contact) of the oblong electrode contacts forming electrodes 18a, 18b, and 18c, 18e, 18g, and 18h. Particular embodiments may include a stimulation lead with electrode contacts having any suitable shapes and sizes, which may be uniform or different, according to particular needs. Some embodiments may include a stimulation lead 14 having electrode contacts that are at least two to four times the size of other electrode contacts of the stimulation lead 14.

In certain embodiments, the use of multiple separate electrode contacts to act as a single electrode 18 and arranged across stimulation lead 14 enhances the ability of stimulation lead 14 to bend or flex, such as transversely across longitudinal axis 19 of stimulation lead 14. If electrode 18d, for example, comprised a single electrode contact arranged across the paddle-shaped stimulating portion in a perpendicular relationship to electrodes 18a, 18b, 18c, 18e, 18g, and 18h, then stimulation lead 14 would be less able to bend or flex transversely about longitudinal axis 19. In addition, the separate electrode contacts of electrodes 18d and 18f in the illustrated embodiment are aligned in rows across stimulation portion 20 to further enhance the ability of stimulation lead 14 to bend or flex transversely about longitudinal axis 19. Particular embodiments may include electrode contacts arranged in any suitable manner to provide increased flexibility of stimulation lead 14 as appropriate or desired.

In certain embodiments, electrodes 18 may be set and arranged as appropriate to provide anode guarding or blocking. As indicated above, current flows from an anode to a cathode. An anode guard functions, in part, to laterally limit an applied electrical field to assist in reducing extraneous stimulation of spinal cord and other tissue surrounding the target spinal cord tissue. In certain embodiments, since a cathode electrode 18 provides the actual stimulation of the target spinal cord tissue (i.e., stimulation occurs at or neat the cathode), one or more anode electrodes 18 may be positioned around or otherwise relative to one or more cathode electrodes 18 to focus an applied electrical field in the vicinity of the one or more cathode electrodes 18. Thus, electrodes 18 set and arranged to provide anode guarding or blocking may enable stimulation lead 14 to apply more focused and therapeutically effective stimulation energy than applied if electrodes were otherwise set or arranged. Setting electrodes 18 to provide anode guarding or blocking may comprise setting individual electrodes 18 as cathodes or anodes in a manner sufficient to provide such functionality, and arranging electrodes 18 to provide anode guarding or blocking may comprise positioning electrodes 18 on stimulation lead 14 in a manner sufficient to provide such functionality.

As indicated above, in particular embodiments, separate electrode contacts may be programmed to function as separate electrodes. In addition, any number of separate electrode contacts may be combined to operate as a single electrode in any suitable manner (e.g., as the three separate electrode contacts of electrode 18f are adapted to operate as a single electrode). The ability to, as is desired, to program separate electrode contacts to operate as one or more electrodes, whether set as cathodes, anodes, or in high impedance, open circuit or "off state," provides great flexibility in stimulating options, particular with respect to anode guarding or blocking functionality.

Figure 2B:
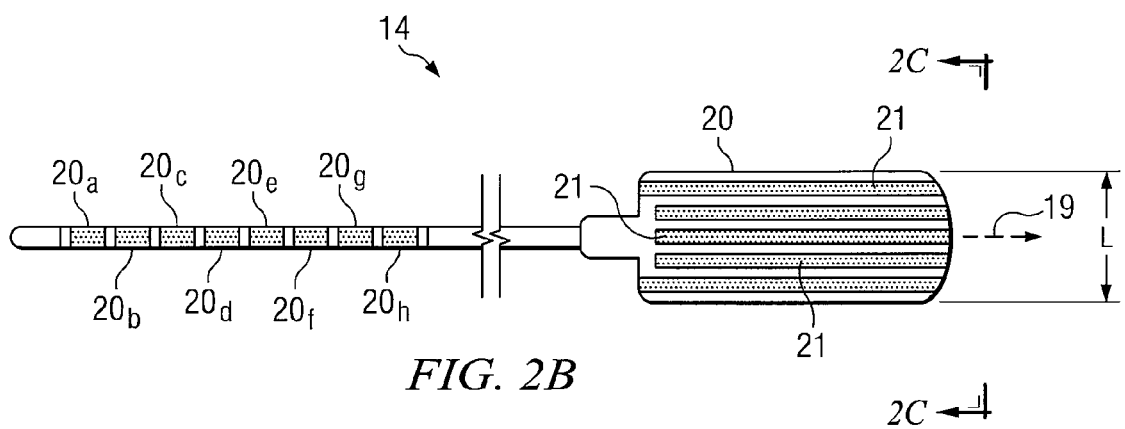

FIG. 2B is an illustration of stimulation lead 14 that shows the underside of stimulation portion 20, or the opposite side of stimulation portion 20 from that shown in FIG. 2A. Stimulating portion 20 includes grooves 21 running the length L of stimulation portion 20. Grooves 21 reduce the area of the underside of stimulating portion 20 contacting tissue. In certain embodiments, grooves 21 aid in stabilizing stimulation lead 14 laterally when stimulation lead is being implanted proximate target spinal cord tissue and thereafter. For example, grooves 21 may help prevent stimulation lead 14 from veering to one side or the other as stimulation lead 14 is advanced along the dorsal column midline during implantation and may further help prevent stimulation lead 14 from slipping to one side of the dorsal column midline stimulation lead 14 has been implanted and thereafter. In certain embodiments, grooves 21 also further enable stimulation lead 14 to bend or flex transversely about longitudinal axis 19. While five grooves 12 are shown, particular embodiments may include any number of grooves 21 arranged in any suitable manner. Preferably, multiple grooves 21 are transversely positioned coincident with the portions of the paddle face that do not include electrical contacts, thereby facilitating the flexing characteristics of lead 14. In an alternative embodiment, grooves 21 can be filled or replaced with longitudinal segments of a polymer material having a reduced durometer relative to insulative material of the remaining portion of the paddle. The selection of the durometer for the longitudinal segments of material can be made to facilitate transverse flexing of the paddle.

Figure 2C:
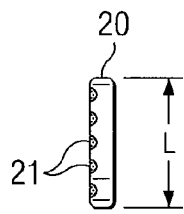

FIG. 2C is a cross-sectional view of stimulating portion 20 taken along line 2C-2C of FIG. 2B. As illustrated, grooves 21 are formed as round cut-outs of stimulation portion 20. However, other embodiments may include grooves 21 having other suitable shapes or configurations.

Figure 3:
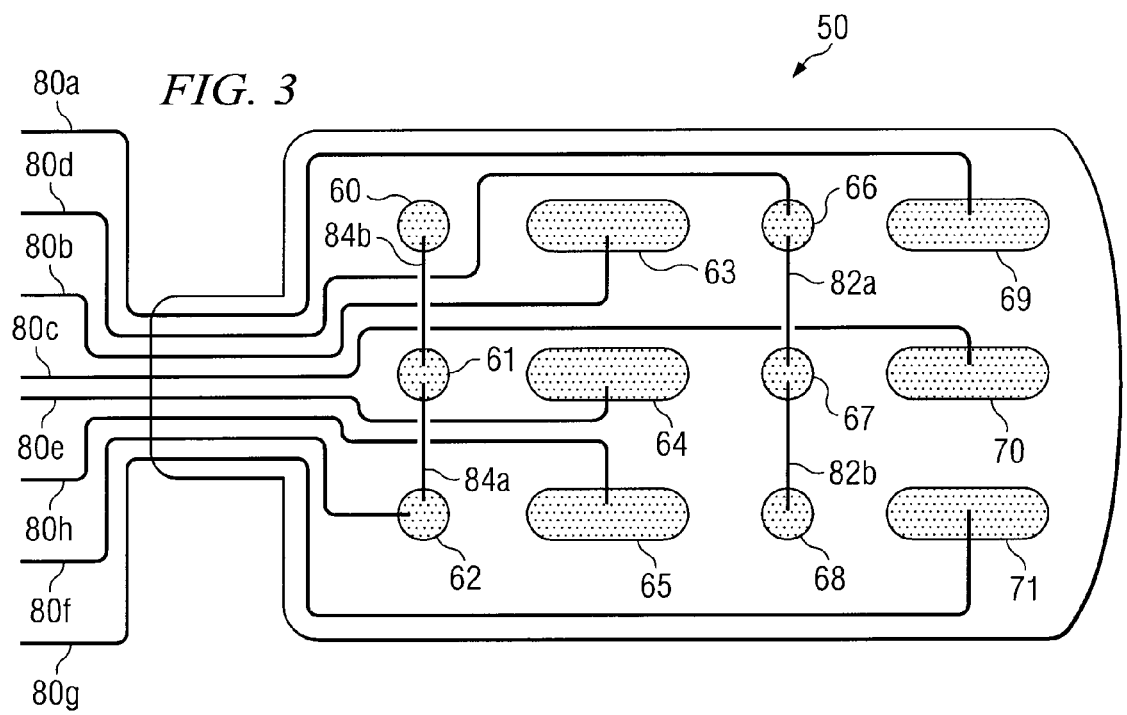
FIG. 3 illustrates a stimulating portion that may be used to electrically stimulate a person's spinal cord tissue to treat one or more clinical conditions showing example electrode contact wiring connections.

FIG. 3 illustrates a stimulating portion 50 that may be used to electrically stimulate a person's spinal cord tissue to treat one or more clinical conditions showing example electrode contact wiring connections. Stimulation portion 50 may be similar to stimulating portion 20 described above in regard to FIGS. 1A, 1B, 2A, 2B and 2C. Stimulation source 50 includes stimulation electrode contacts 60-71 having varying shapes and sizes. In the illustrated embodiment, electrode contacts 60-62 and 66-68 are generally round and each have a size approximately three-fourths the size of each oblong electrode contact 63-65 and 69-71.

The illustrated embodiment includes electrical conductors 80a-80h coupled to electrode contacts 60-71. Electrical conductors 80a-80h may be coupled to terminals coupled to a stimulation source, such as terminals 20a-20h, respectively of FIGS. 2A and 2B. Electrical conductors 80a-80h transmit stimulation pulses from a stimulation source to electrode contacts 60-71. The actual connections of electrical conductors to electrode contacts may implemented in any suitable manner, such as physically connecting electrode conductors to portions of electrode contacts on the underside of such contacts exposed through the underside of stimulation face of stimulation portion 50.

As indicated above, electrode contacts of a stimulating portion in accordance with various embodiments may be coupled to terminals in any suitable manner. FIG. 3 illustrates one example of such coupling. As illustrated, electrical conductor 80a is coupled to electrode contact 69; electrical conductor 80b is coupled to electrode contact 63; electrical conductor 80c is coupled to electrode contact 70; electrical conductor 80d is coupled to electrode contact 66; electrical conductor 80e is coupled to electrode contact 64; electrical conductor 80f is coupled to electrode contact 62; electrical conductor 80g is coupled to electrode contact 71; and electrical conductor 80h is coupled to electrode contact 65.

In addition, stimulation portion includes conductors 82a-82b and 84a-84b. Electrical conductor 82a couples electrode contact 66 with electrode contact 67 and electrical conductor 82b couples electrode contact 67 with electrode contact 68. Thus, since electrode contacts 66-68 are each coupled together (e.g., through electrical conductors 80d, 82a, and 82b), they may be operatively set to function as one electrode. In addition, electrical conductor 84a couples electrode contact 61 with electrode contact 62 and electrical conductor 84b couples electrode contact 60 with electrode contact 61. Thus, since electrode contacts 60-62 are each coupled to together (e.g., through electrical conductors 80f, 84a, and 84b), they may be operatively set to function as one electrode.

Thus, the wiring of the illustrated embodiment is such that stimulation portion 50 includes electrode contacts that may function as eight separate electrodes. Electrode contacts 63-65 and 69-71 may function as six separate electrodes. Electrode contacts 63-65 and 69-71 may function as a single electrode and electrode contacts 66-68 may function as a single electrode. As indicated above, stimulating portions of other embodiments may include electrode contacts wired to function as any number or type of electrodes.

Figure 5:
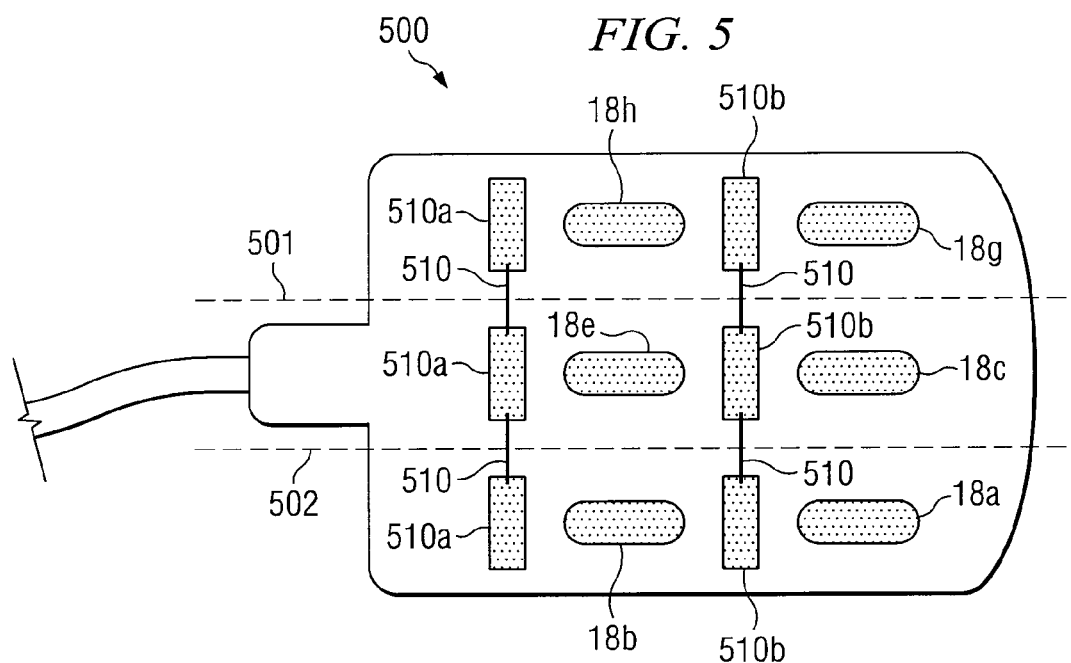
FIGS. 5-7 depict respective stimulation paddle designs according to alternative embodiments.

FIG. 5 depicts an alternative paddle design according to one representative embodiment. As shown in FIG. 5, paddle lead 500 comprises electrode contacts 18a, 18b, 18c, 18e, 18h, and 18g implemented in substantially the same manner as the electrode contacts of stimulation portion 20 shown in FIG. 2A. Each of these electrode contacts are preferably separately coupled to different conductors of the lead to allow these contacts to independently function in cathode, anode, or high impedance states. Preferably, grooves 21 (previously shown in FIG. 2B) are disposed on the other side of paddle lead 500 to facilitate the flexibility of the paddle structure of lead 500.

The electrode contact design of paddle lead 500 differs from the design shown in FIG. 2A with regard to the electrode contacts intended to perform anodal blocking. Specifically, electrodes 510a and 510b are respectively formed of three separate bar-shaped electrode contacts. The separate electrode contacts occupy more surface area than the corresponding electrode contacts of stimulation portion 20. However, the separate electrode contacts are spaced apart by sufficient space to enable the paddle structure to transversely flex at locations 501 and 502. To electrically couple each of the separate electrode contacts together, a trace or strip of flexible conductive epoxy 510 is placed between the separate electrode contacts. Additionally, the trace or strip of epoxy material 510 is oriented in a transverse direction on the paddle structure to facilitate the flexibility of the paddle at locations 501 and 502. The traces or strips 510 of conductive epoxy can be overlaid with suitable bio-compatible, bio-stable polymer depending upon the characteristics of the selected epoxy material.

A thin film conductor can be utilized for traces or strips 510 according to an alternative embodiment. The thin film conductor traces can be formed in multiple layers. For example, a first thin metal layer can be formed on the polymer substrate of the paddle structure using titanium, chromium, aluminum or nickel. To enhance adherence of this coating to the polymer material, the coating is either concurrently bombarded during its deposition by high energy ions, which serve to "shot-peen" the film layer into the surface of the polymer and to continuously break up the coating from an amorphous/columnar structure to a nanocrystalline structure, exhibiting over-lapping platelet regions. The concurrent bombardment is commonly referred to by the acronym "IBAD" for ion beam assisted deposition. Alternatively, so-called ion beam enhanced deposition or IBED may be used where ion beam bombardment is applied subsequent to the deposition of the metallic layer.

A second thin metal film layer or coating is subsequently deposited over the first layer using palladium or platinum to function as a self-alloying/oxygen diffusion barrier layer. The deposition preferably takes place in the presence of high energy ions to enhance stitching between the base layer and the second layer to provide a desired stress-free and non-columnar structure. A third metal film layer is then applied to a predetermined thickness to function as a bulk conductive layer. The third metal layer preferably comprises platinum or silver or another similar conductive element or alloy. A final bio-compatible, bio-stable conductive layer is applied for exposure to the tissue of the patient. By minimizing the thickness of the conductive traces and by orienting the traces transversely on the paddle, paddle lead 600 is able to flex about locations 501 and 502.

Figure 6:
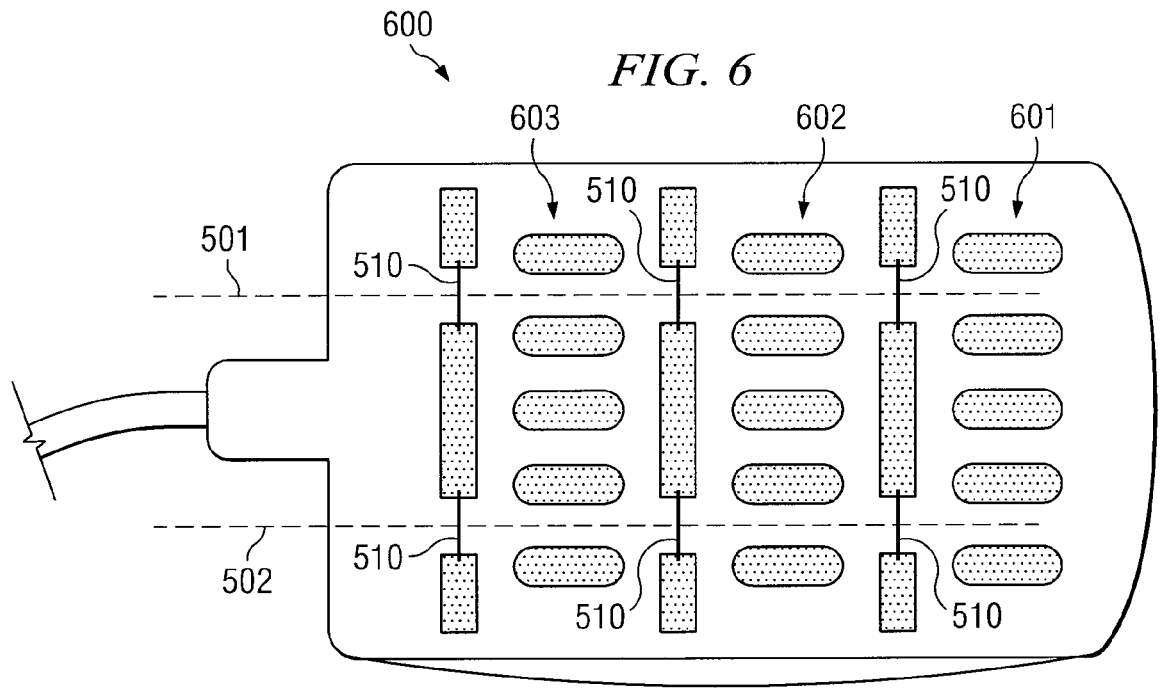
Figure 7:
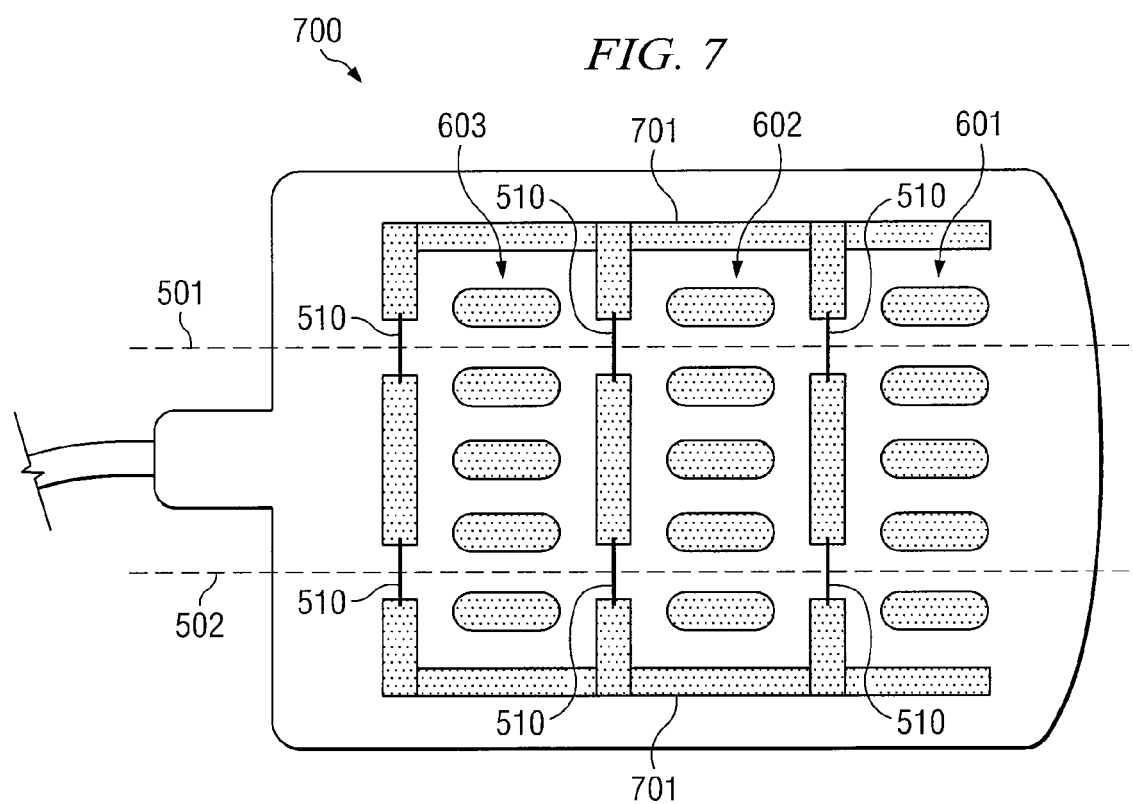

FIG. 6 depicts paddle lead 600 according to another representative embodiment. Paddle lead 600 is preferably implemented in a manner that is substantially similar to paddle lead 500 except paddle lead 600 includes multiple rows 601, 602, and 602 of independent electrode contacts (in this embodiment, there are five independent electrode contacts per row). FIG. 7 depicts paddle lead 700 that is substantially the same as paddle lead 600 except that paddle lead 700 comprises longitudinal electrode contacts 701 on the edges of the paddle structure to perform lateral anode blocking as appropriate for a given therapeutic application. The multiple rows 601, 602, and 603 of paddle leads 600 and 700 are advantageous in that the various rows can be used substantially independently to address complex pain patterns in a substantially simultaneous manner. For example, row 601 could be utilized to treat chronic pain in a first limb and row 603 could be utilized to treat chronic pain in a second limb. Anodal blocking may occur between the two rows 601 and 603 to substantially cause the electrical fields associated with those rows to be independent from each other. Additionally, the greater number of electrodes in a given row enables greater freedom in steering an applied electrical field in the transverse direction as necessary for a particular patient and pain condition.

Figure 4:
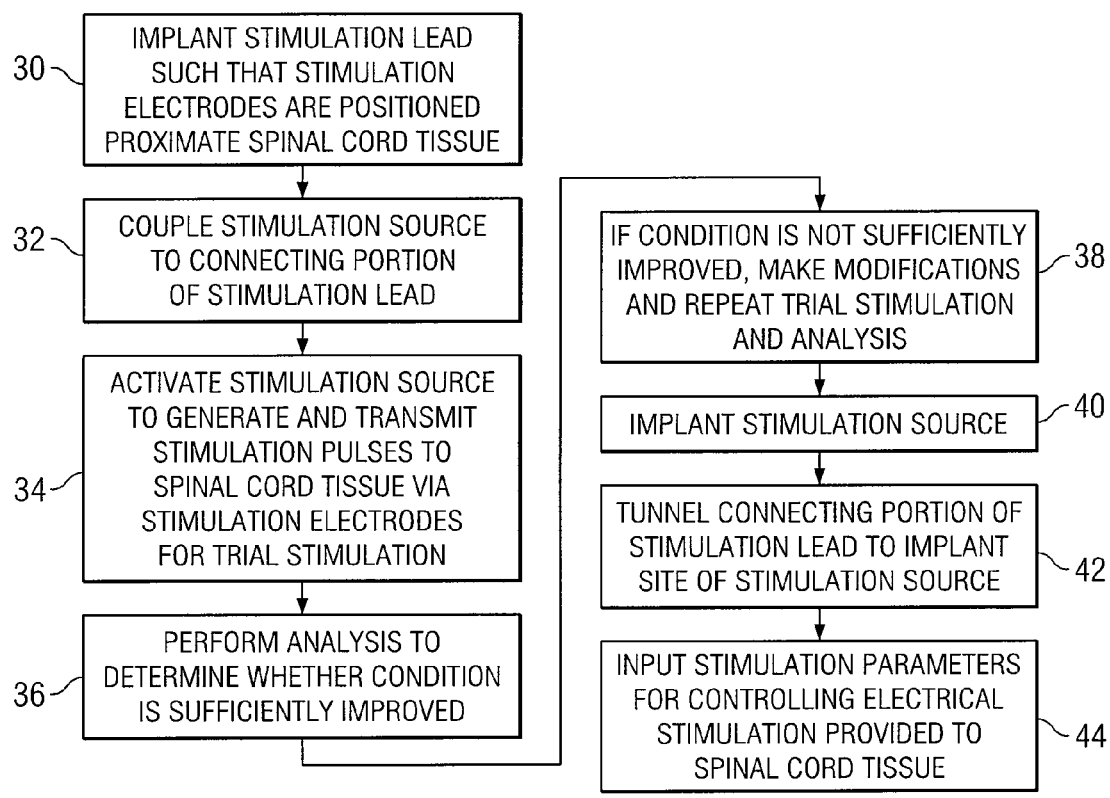
FIG. 4 illustrates an example method of implanting the stimulation systems of FIGS. 1A and 1B into a person's body with a stimulation lead located proximate spinal cord tissue for electrical stimulation to treat one or more clinical conditions.

FIG. 4 illustrates an example method of implanting stimulating system 10 of FIGS. 1A-1B into a person's body with stimulation lead 14 located proximate target spinal cord tissue for electrical stimulation to treat one or more clinical conditions, such as chronic pain. At step 30, stimulation lead 14 is implanted such that one or more electrodes 18 of stimulation lead 14 are positioned proximate target spinal cord tissue. Techniques for implanting stimulation leads such as stimulation lead 14 are known to those skilled in the art. At step 32, stimulation source 12 may be coupled directly to connecting portion 16 of stimulation lead 14. Alternatively, as described above, stimulation source 12 may not be coupled directly to stimulation lead 14 and may instead be coupled to stimulation lead 14 via a wireless link.

Intra-implantation trial stimulation may be conducted at steps 34-38. Alternatively, the method may proceed from step 32 to 40. At step 34, stimulation source 12 is activated to generate and transmit stimulation pulses to the target spinal cord tissue via one or more electrodes 18 of stimulation lead 14 positioned proximate the target spinal cord tissue. At step 36, subjective or objective testing and analysis may be performed to determine whether one or more clinical conditions are sufficiently improved, one or more stimulation patterns may be adjusted, stimulation lead 14 may be moved incrementally or even re-implanted, or both of these modifications may be made at step 38 and the trial stimulation and analysis repeated until the one or more clinical conditions are sufficiently improved. Once the stimulation parameters have been properly set and stimulation lead 14 has been properly positioned such that the one or more clinical conditions are sufficiently improved, intra-implantation trial stimulation is complete.

Once stimulation lead 14 has been properly implanted and secured, and any trial stimulation completed, stimulation source 12 is implanted as step 40. Techniques for implanting stimulation source 12 are known to those skilled in the art. The implant site is typically a subcutaneous pocket formed to receive and house stimulation source 12. The implant site is usually located some distance away from the insertion site, such as in or near the upper chest or buttocks. Where stimulation lead 14 includes connecting portion 16, connecting portion 16 is tunneled, at least in part, subcutaneously to the implant site of stimulation source 12 at step 42. At step 44, a doctor, the patient, or another user of stimulation source 12 may directly or indirectly input stimulation parameters for controlling the nature of the electrical stimulation provided to the target spinal cord tissue, if not already set during any intra-implantation trial stimulation period. When appropriate, post-implantation trail stimulation may be conducted, over one or more weeks or months for example, and any necessary modifications made accordingly.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

The invention claimed is:

1. A paddle lead for implantation within the body of a patient for delivering therapeutic electrical stimulation energy to target spinal cord tissue of the patient, the paddle lead comprising:
   a stimulation paddle including a first insulative material;
   a plurality of electrode contacts disposed on a first side of the stimulation paddle of the paddle lead, the plurality of electrode contacts being adapted to allow the stimulation paddle to flex transversely about a longitudinal axis of the stimulation paddle;
   a plurality of grooves disposed on a second side of the stimulation paddle opposite to the first side, the plurality of grooves disposed substantially parallel to the longitudinal axis, the plurality of grooves running along a substantial portion of a length of the stimulation paddle;
   at least one of the plurality of grooves including a segment of a second insulative material with the second insulative material being of reduced durometer relative to the first insulative material of the stimulation paddle;
   a plurality of conductors for conducting electrical energy to the plurality of electrode contacts;
   wherein the plurality of electrode contacts are arranged in at least first, second, and third rows that are disposed perpendicular to the longitudinal axis of the stimulation paddle;
   the first and third rows respectively having multiple electrode contacts electrically coupled to different conductors of the plurality of conductors to enable the multiple electrode contacts of the first and third rows to function in independent cathode states, anode states, or high-impedance states;
   the second row being disposed between the first and third rows, the second row having multiple electrode contacts each electrically coupled to a common conductor of the plurality of conductors to cause the multiple electrode contacts of the second row to function in a common cathode state, anode state, or high-impedance state.

2. The paddle lead of claim 1 wherein the multiple electrode contacts of the second row are further disposed in multiple columns such that the plurality of electrical contacts do not enter multiple longitudinal areas of the first side of the stimulation paddle such that the stimulation paddle flexes at the multiple longitudinal areas.

3. The paddle lead of claim 2 wherein at least some of the plurality of grooves are disposed opposite to respective ones of the multiple longitudinal areas to facilitate transverse flexing of the stimulation paddle.

4. The paddle lead of claim 1 wherein the multiple electrode contacts of the second row are electrically connected by exposed flexible conductive traces between the electrical contacts.

5. The paddle lead of claim 4 wherein the exposed conductive traces comprise multiple thin layers of conductive material.

6. The paddle lead of claim 4 wherein the exposed flexible conductive traces are disposed in a direction transverse to the longitudinal axis of the stimulation paddle.

7. The paddle lead of claim 1 wherein the multiple electrode contacts of the second row are electrically coupled by a flexible conductive epoxy material disposed between the electrode contacts of the second row.

8. The paddle lead of claim 7 wherein the flexible conductive epoxy material is disposed in thin stripes, between the electrode contacts of the second row, that are oriented in a direction transverse to the longitudinal axis of the stimulation paddle.

9. The paddle lead of claim 1 wherein each electrode contact of the second row possesses a surface area of approximately three-fourths of the surface area of electrode contacts of the first and third rows.

10. The paddle lead of claim 1 wherein the first and third rows comprise at least five independent electrode contacts.

11. The paddle lead of claim 1 further comprising:
 a first longitudinally oriented electrode extending from at least the first row to the third row on a first edge of the stimulation paddle; and
 a second longitudinally oriented electrode extending from at least the first row to the third row on a second edge of the stimulation paddle.

12. A system for implantation within the body of a patient for delivering therapeutic electrical stimulation energy to target spinal cord tissue of the patient, the system comprising:
 an implantable pulse generator (IPG) for generating electrical pulses; and
 a paddle lead for delivering electrical pulses from the IPG to target spinal cord tissue, the paddle lead comprising:
  a stimulation paddle including a first insulative material;
  a plurality of electrode contacts disposed on a first side of the stimulation paddle of the paddle lead, the plurality of electrode contacts being adapted to allow the stimulation paddle to flex transversely about a longitudinal axis of the stimulation paddle;
  a plurality of grooves disposed on a second side of the stimulation paddle opposite to the first side, the plurality of grooves disposed substantially parallel to the longitudinal axis, the plurality of grooves running along a substantial portion of a length of the stimulation paddle;
  at least one of the plurality of grooves including a segment of a second insulative material with the second insulative material being of reduced durometer relative to the first insulative material of the stimulation paddle;
  a plurality of conductors for conducting electrical energy from a plurality of terminals to the plurality of electrode contacts;
  wherein the plurality of electrode contacts are arranged in at least first, second, and third rows that are disposed perpendicular to the longitudinal axis of the stimulation paddle;
  the first and third rows respectively having multiple electrode contacts electrically coupled to different conductors of the plurality of conductors to enable the multiple electrode contacts of the first and third rows to function in independent cathode states, anode states, or high-impedance states;
  the second row being disposed between the first and third rows, the second row having multiple electrode contacts each electrically coupled to a common conductor of the plurality of conductors to cause the multiple electrode contacts of the second row to function in a common cathode state, anode state, or high-impedance state.

13. The system of claim 12 wherein the IPG is programmed to deliver first electrical pulses to target spinal cord tissue on the first row and to deliver second electrical pulses to target spinal cord tissue on the third row to address chronic pain in distinct locations of the body.

14. The system of claim 13 wherein the IPG is programmed to anodally block the first and second electrical pulses by setting the electrical contacts of the second row to an anode state when the first and second electrical pulses are delivered to the first and third rows.

15. The system of claim 12 wherein the multiple electrode contacts of the second row are electrically connected by exposed flexible conductive traces between the electrical contacts.

16. The system of claim 15 wherein the exposed flexible conductive traces comprise multiple thin layers of conductive material.

17. The system of claim 15 wherein the exposed flexible conductive traces are disposed in a direction transverse to the longitudinal axis of the stimulation paddle.

18. The system of claim 12 wherein the multiple electrode contacts of the second row are electrically coupled by a flexible conductive epoxy material disposed between the electrode contacts of the second row.

19. The system of claim 18 wherein the flexible conductive epoxy material is disposed in thin stripes, between the electrode contacts of the second row, that are oriented in a direction transverse to the longitudinal axis of the stimulation paddle.

20. The system of claim 12 wherein each electrode contact of the second row possesses a surface area of approximately three-fourths of the surface area of electrode contacts of the first and third rows.

21. The system of claim 12 wherein the first and third rows comprise at least five independent electrode contacts.

22. The system of claim 12 further comprising:
 a first longitudinally oriented electrode extending from at least the first row to the third row on a first edge of the stimulation paddle; and
 a second longitudinally oriented electrode extending from at least the first row to the third row on a second edge of the stimulation paddle.

* * * * *

UNITED STATES PATENT AND TRADEMARK OFFICE
CERTIFICATE OF CORRECTION

PATENT NO. : 7,603,178 B2  Page 1 of 1
APPLICATION NO. : 11/279712
DATED : October 13, 2009
INVENTOR(S) : North et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 823 days.

Signed and Sealed this

Fifth Day of October, 2010

David J. Kappos
*Director of the United States Patent and Trademark Office*